(12) United States Patent
Rucker

(10) Patent No.: US 9,839,761 B1
(45) Date of Patent: Dec. 12, 2017

(54) AIRFLOW CONTROL FOR PRESSURIZED AIR DELIVERY

(71) Applicant: Hal Rucker, Hillsborough, CA (US)

(72) Inventor: Hal Rucker, Hillsborough, CA (US)

( * ) Notice: Subject to any disclaimer, the term of this patent is extended or adjusted under 35 U.S.C. 154(b) by 810 days.

(21) Appl. No.: 14/313,257

(22) Filed: Jun. 24, 2014

Related U.S. Application Data

(60) Provisional application No. 61/843,025, filed on Jul. 4, 2013.

(51) Int. Cl.
*A62B 9/02* (2006.01)
*A61M 16/20* (2006.01)
*A61M 16/00* (2006.01)
*A61M 16/06* (2006.01)

(52) U.S. Cl.
CPC ...... *A61M 16/207* (2014.02); *A61M 16/0057* (2013.01); *A61M 16/06* (2013.01)

(58) Field of Classification Search
CPC ............ A61B 9/00; A61M 16/00; A61M 16/06–16/0694; A61M 16/20–16/209; A62B 7/00; A62B 7/04; A62B 7/14; A62B 18/00; A62B 18/10; B63C 11/12; B63C 11/18
See application file for complete search history.

(56) References Cited

U.S. PATENT DOCUMENTS

| | | | | |
|---|---|---|---|---|
| 4,436,277 A | * | 3/1984 | Robak | F16K 7/06 251/6 |
| 6,228,048 B1 | * | 5/2001 | Robbins | A61M 3/0241 604/27 |
| 7,487,778 B2 | | 2/2009 | Freitag | |
| 7,533,670 B1 | | 5/2009 | Freitag et al. | |
| 7,643,685 B2 | | 1/2010 | Miller | |
| 7,827,038 B2 | | 11/2010 | Richard et al. | |
| 7,856,983 B2 | | 12/2010 | Blom | |
| 7,997,272 B2 | | 8/2011 | Isaza | |
| 8,161,972 B2 | | 4/2012 | Isaza | |
| 8,236,216 B2 | | 8/2012 | Thornton | |
| 8,254,637 B2 | | 8/2012 | Abourizk et al. | |
| 8,327,851 B2 | | 12/2012 | Connor | |
| 8,418,694 B2 | | 4/2013 | Freitag et al. | |
| 2004/0034298 A1 | | 2/2004 | Johnson et al. | |
| 2006/0023228 A1 | | 2/2006 | Geng | |
| 2006/0049371 A1 | * | 3/2006 | Ohnishi | F16K 7/04 251/7 |
| 2006/0235877 A1 | | 10/2006 | Richard et al. | |
| 2008/0060646 A1 | | 3/2008 | Isaza | |
| 2008/0060652 A1 | | 3/2008 | Selvarajan et al. | |
| 2008/0060656 A1 | | 3/2008 | Isaza | |
| 2009/0065005 A1 | | 3/2009 | Ades | |
| 2009/0107494 A1 | | 4/2009 | Freitag et al. | |
| 2009/0205662 A1 | | 8/2009 | Kwok et al. | |
| 2009/0255533 A1 | | 10/2009 | Freitag et al. | |
| 2009/0293875 A1 | | 12/2009 | Kwok et al. | |
| 2010/0258133 A1 | | 10/2010 | Todd et al. | |
| 2010/0269834 A1 | | 10/2010 | Freitag et al. | |

(Continued)

*Primary Examiner* — Todd J Scherbel
*Assistant Examiner* — Ned T Heffner
(74) *Attorney, Agent, or Firm* — Patent Law Offices Michael E. Woods; Michael E. Woods

(57) ABSTRACT

A system and method for airflow control of pressurized air delivery, and more specifically, but not exclusively, to a robust valve assembly for use in a positive airway pressure treatment (PAPT) system and method to improve speech during treatment.

13 Claims, 16 Drawing Sheets

(56) References Cited

U.S. PATENT DOCUMENTS

| | | |
|---|---|---|
| 2011/0132375 A1 | 6/2011 | Thornton |
| 2011/0186045 A1 | 8/2011 | Erickson |
| 2011/0259339 A1 | 10/2011 | Isaza |
| 2012/0055471 A1 | 3/2012 | Hadas et al. |
| 2012/0305003 A1 | 12/2012 | Mark |
| 2013/0118498 A1 | 5/2013 | Robitaille et al. |
| 2013/0139820 A1* | 6/2013 | Haibach ................ A61M 16/06 128/205.24 |

* cited by examiner

AIRFLOW CONTROL FOR PRESSURIZED AIR DELIVERY

CROSS REFERENCE TO RELATED APPLICATIONS

This application claims benefit of U.S. patent application Ser. No. 61/843,025, the contents of which are hereby expressly incorporated in its entirety by reference thereto for all purposes.

FIELD OF THE INVENTION

The present invention relates generally to airflow control for pressurized air delivery, and more specifically, but not exclusively, to a robust valve assembly for use in a positive airway pressure treatment (PAPT) system and method to improve speech during treatment.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Sleep apnea is a common disorder in which a person experiences one or more breathing disruptions while sleeping. Those disruptions may include one or more pauses and/or one or more shallow breaths. Breathing pauses may last from a few seconds to minutes, and may occur 30 times or more in any given hour. A common type of sleep apnea is obstructive sleep apnea in which a person's airway collapses or becomes blocked during sleep. This collapse/blockage causes the breathing disruption. Sleep apnea is a dangerous sleep disorder that can cause negative health consequences when left untreated.

Positive airway pressure treatment (PAPT), of which continuous positive airway pressure (CPAP) is an example, is a treatment modality that uses mild positive air pressure to open the breathing airways. In addition to CPAP, other types of continuous positive airway pressure treatment include Bilevel Positive Airway Pressure (BIPAP) and variable positive airway pressure (VPAP). PAPT typically is used by people who have breathing disruptions, such as sleep apnea. PAPT treatment involves use of a PAPT treatment system, which has three main parts: 1) a mask or other device that fits over the nose or the nose and mouth; 2) a motor that blows air; and 3) a tube that connects the mask to the motor. The blowing air generates the positive air pressure that keeps the airways open during sleeping.

While wearing a PAPT device that applies positive pressure to a patient, the pressure interferes with speech and other vocalizations during treatment. Temporarily suspending treatment, such as by turning off the device or removing the mask to enable the patient to be clearly understood, is undesirable for a number of reasons. One reason it is undesirable to turn off the machine is that doing so can reset a treatment profile being used for the patient. A reason it is undesirable to remove the mask temporarily is because it can be a challenging/time-consuming task to properly seat and adjust the mask for proper operation and comfort. A patient will typically elect to continue treatment while participating in certain types of verbal exchanges (e.g., expression of "good night" wishes to a partner, children, or others nearby). The difficulty of speaking and frustrations of the possibility of not being clearly understood while wearing a conventional mask during treatment is undesirable.

What is needed is a system and method for improving speech during positive airway pressure treatment.

BRIEF SUMMARY OF THE INVENTION

Disclosed is a system and method for improving speech during positive airway pressure treatment (PAPT).

The following summary of the invention is provided to facilitate an understanding of some of technical features related to valve assemblies used in PAPT, and is not intended to be a full description of the present invention. A full appreciation of the various aspects of the invention can be gained by taking the entire specification, claims, drawings, and abstract as a whole. The present invention is applicable to other pressure systems worn by a person, including respiratory systems and methods employed for respiratory therapy and treatment, such for asthma, chronic obstructive pulmonary disease (COPD), and tracheostomy alternatives provided by respiratory devices, and the like.

An improved positive airway pressure treatment (PAPT) ventilation system incorporates airflow control. The PAPT ventilation system includes a PAPT mask, a pressure generator, a pressure delivery structure (e.g., a pressure hose), and a valve disposed between the PAPT mask and the pressure delivery structure. (In some implementations, the valve may be disposed elsewhere, for example between the pressure generator and the pressure delivery structure.) The valve enables selective and temporary suspension of pressurized air delivery to the mask which allows the wearer to speak coherently without stopping the pressure generator or removing the PAPT mask. The valve is a special construction, a single inner elastomeric structure disposed within a hard shell.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 13 and FIG. 14 illustrate an integration of the PAPT airflow valve with a hose;

FIG. 13 illustrates an outline of the integration with a hose;

FIG. 14 illustrates a longitudinal section of the integration illustrated in FIG. 13;

FIG. 15-FIG. 17 illustrate an integration of the PAPT airflow valve with different mask implementations;

FIG. 15 illustrates an outline of the integration with a first mask type;

FIG. 16 illustrates an outline of the integration with a second mask type;

FIG. 17 illustrates an outline of the integration with a third mask type;

FIG. 18 illustrates a schematic sectional end view of the actuating element of FIG. 7 without the interlocking ribs;

FIG. 19 illustrates a schematic sectional end view of a collapse of the actuating element of FIG. 9;

FIG. 20 illustrates a cross section of an elastomeric structure;

FIG. 21 illustrates a specification of a nominal inside air channel; and

FIG. 22 illustrates a specification of a pair of opposing vertices and four tangential line segments joining the vertices to the nominal inside air channel producing the eye-shaped section.

DETAILED DESCRIPTION OF THE INVENTION

Figure 1:
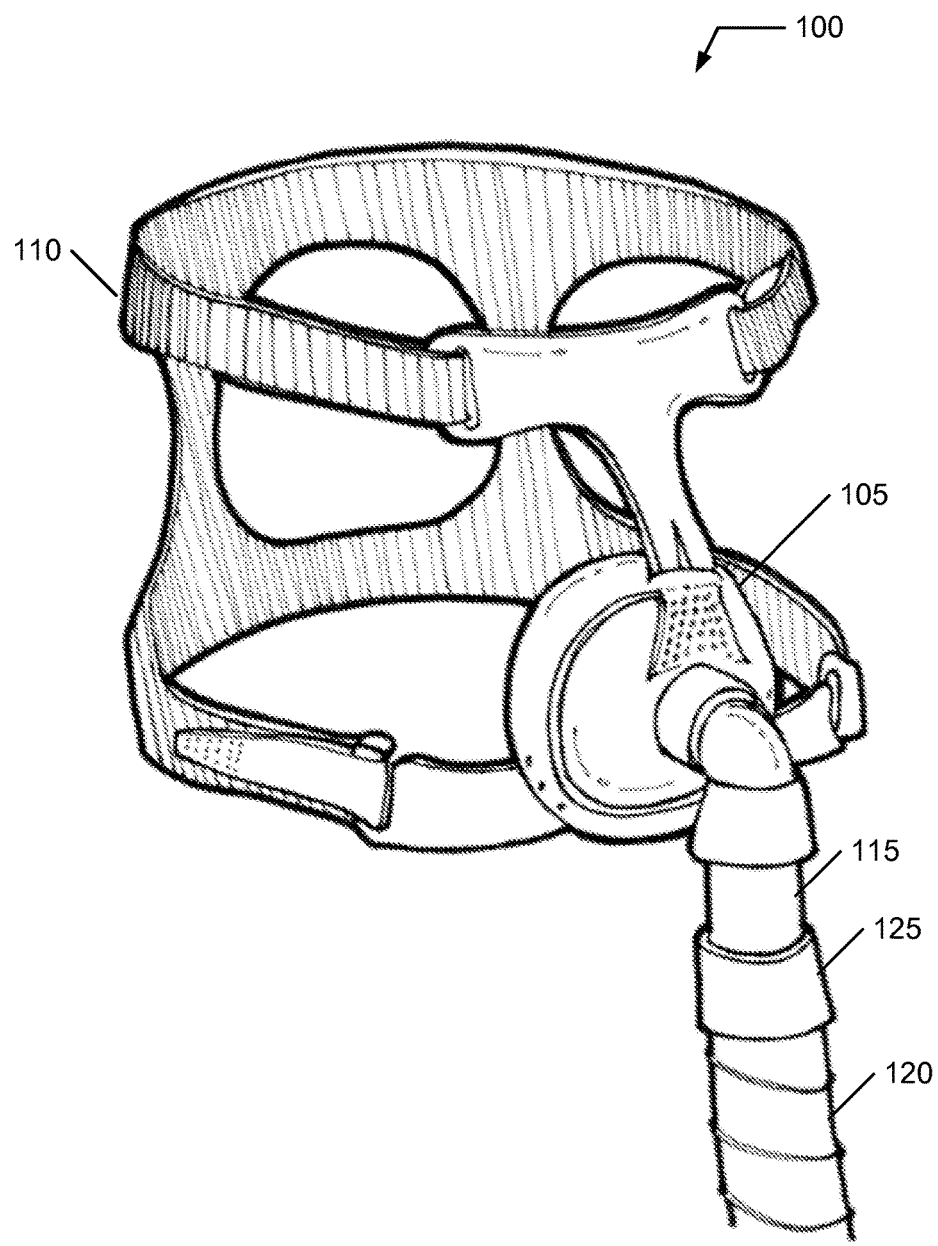
FIG. 1 illustrates a conventional CPAP mask assembly.

Embodiments of the present invention provide a system and method for improving speech during positive airway pressure treatment (PAPT). The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

The following definitions apply to some of the aspects described with respect to some embodiments of the invention. These definitions may likewise be expanded upon herein.

As used herein, the term "or" is generally intended to mean "and/or" unless otherwise indicated.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the term positive air pressure treatment (PAPT) refers to a respiratory treatment in which air is delivered to a patient at a pressure greater than ambient. The delivery mechanism is typically performed using a source of pressurized air or other breathable gas delivered to a respirator (e.g., a mask) by a flexible conduit (e.g., a hose). The source may include a pressurized container or a machine including a compressor system. The pressurized air interferes with some function of the patient (e.g., speaking) and there is a desire to selectively, efficiently, and temporarily relieve and/or eliminate the interference.

As used herein, the terms "optional" and "optionally" mean that the subsequently described event or circumstance may or may not occur and that the description includes instances where the event or circumstance occurs and instances in which it does not.

FIG. 1 illustrates a conventional continuous positive air pressure (CPAP) mask assembly 100. CPAP mask assembly 100 includes a mask 105, a set of straps 110, and a hose coupler 115. Mask 105 is a flexible "one size fits all" covering. Mask 105 is a one-piece construction sized to encompass a nose or a nose and mouth of a wearer. Set of straps 110 engage mask 105 and various portions of a head of the wearer to hold mask 105 in the desired location on the wearer's face.

Hose coupler 115 provides a mechanical interface between a hose 120 and mask 105 by removably attaching to a hose connector 125. Hose connector 125 is complementary to hose coupler 115. In the illustrated embodiment, hose coupler 115 is a "male" connector for engagement with hose connector 125 configured as a "female" structure. Hose coupler 115 hangs off of a front and center portion of mask 105. CPAP mask assembly 100 includes an exhaust valve in mask 105 or hose coupler 115 that expels air in a direction that is directly in front of the wearer and thus toward any person or object the wearer is facing.

Figure 2:
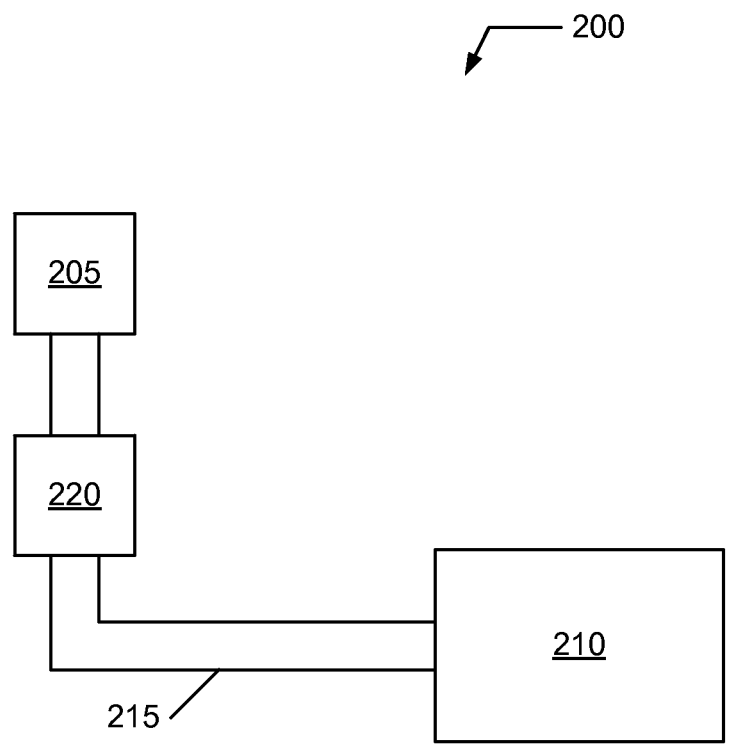
FIG. 2 illustrates a schematic diagram of a switched PAPT system.

FIG. 2 illustrates a schematic diagram of an improved positive airway pressure treatment (PAPT) ventilation system 200 incorporating airflow control. PAPT ventilation system 200 includes a PAPT mask 205, a pressure generator 210, a pressure delivery structure 215, and a valve 220 disposed between PAPT mask 205 and pressure delivery structure 215. (In some implementations, valve 220 may be disposed between pressure generator 210 and pressure delivery structure 215.) Further details of valve 220 are illustrated in FIG. 3-FIG. 22 and described herein PAPT mask 205 applies/delivers a continuous positive pressure to a user. The continuous positive pressure is created by pressure generator 210 which is a sophisticated machine that may provide one or more features such as auto pressure adjusting technology, built-in heater/humidifier, anti-back-flow humidifier, built-in alarm clock, a display for on screen sleep events data, and components for leak compensation and auto altitude adjustments, among other features. Pressure delivery structure 215 is a flexible conduit having one or more air channels to couple and deliver the continuous positive pressure, and processed (e.g., heated and/or humidified) air between pressure generator 210 and PAPT mask 205. In some implementations, pressure delivery structure 215 includes a soft, flexible, non-kinking hose. Valve 220 provides airflow control allowing the user to temporarily stop airflow from pressure generator 210 and PAPT mask 205 and thereby easily speak as long as the airflow is suspended. When the need or desire to speak coherently and/or comfortably passes, the user releases valve 220 and airflow is resumed.

Pressure generator 210 is able to generate a range of appropriate pressure ranges for effective treatment of sleep apnea, for example 3 cm $H_2O$ to 25 cm $H_2O$, at 15 to 75 liters of air per minute. Other pressures and airflow rates are within the scope of the present invention. Valve 220 safely, reliably, simply, efficiently, silently, and robustly stops this airflow for as long as the user desires. Releasing valve 220 automatically returns it to full airflow rate.

Figure 3:
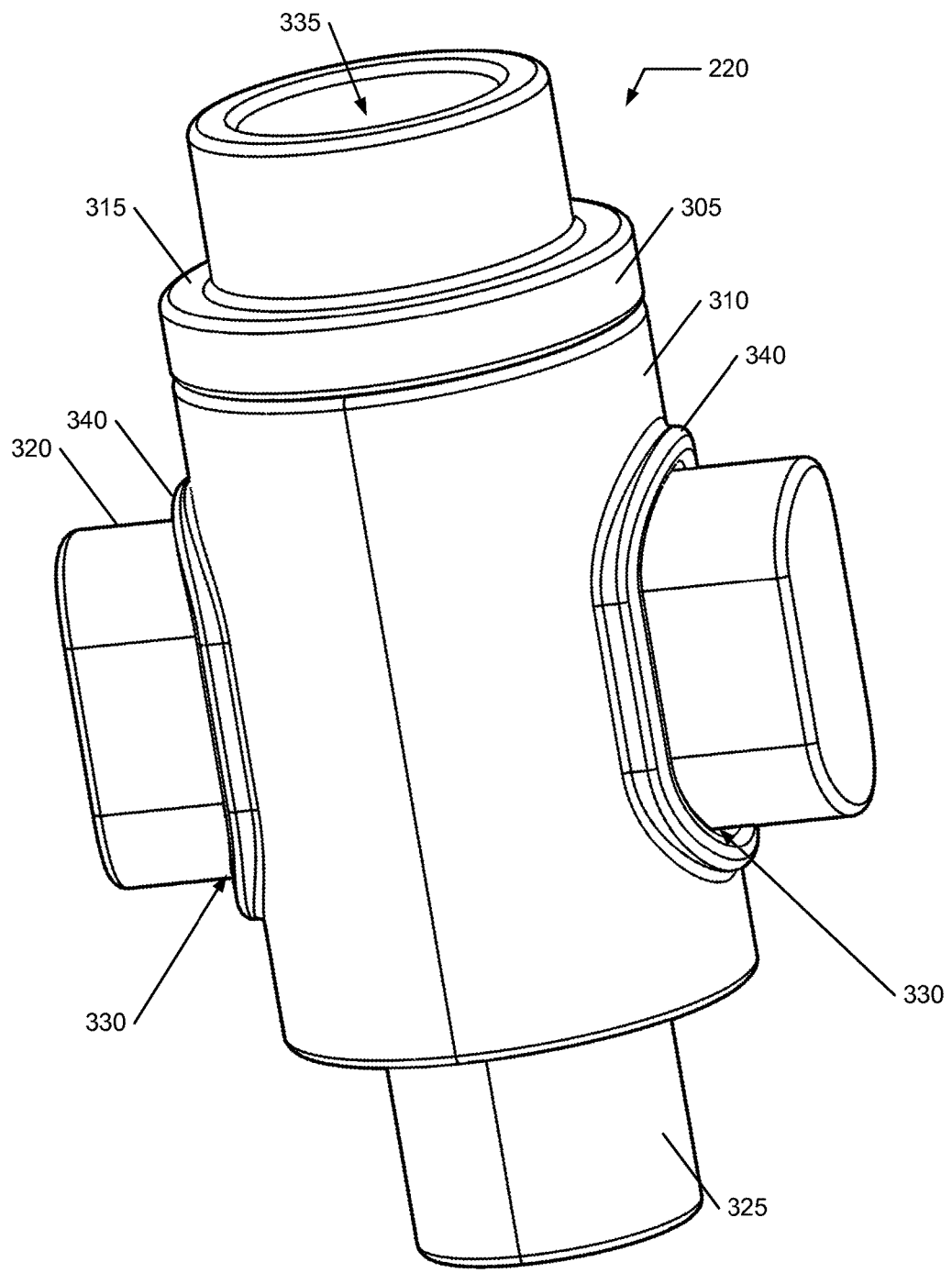
FIG. 3 illustrates a perspective view schematic of an improved PAPT airflow valve.

FIG. 3 illustrates a perspective view schematic of improved PAPT airflow valve 220. Valve 220 includes an actuating element 305 and an external housing shell 310. Actuating element 305 is a single molded, flexible, elastomeric structure that includes a valve connector 315 and a pair of opposing actuating buttons 320 that extend from external housing shell 310. Valve connector 315 is complementary to hose coupler 115 and functionally emulates hose connector 125 to form an airtight seal with mask 105.

External housing shell 310 is a rigid plastic structure (e.g., polystyrene, acetates, celluloids, resins, vinyls, nylons, organic polymers, other hard plastics, and the like may be used) that includes a valve coupler 325 extending opposite of valve connector 315 and a pair of opposing lateral apertures 330. Apertures 330 accommodate the opposing actuating buttons 320 that extend outside through external housing shell 310. Valve coupler 325 is complementary to hose connector 125 and functionally emulates hose coupler 115 to form an airtight seal with hose 120.

A collapsible air channel 335 extends through valve 220 between valve connector 315 and valve coupler 325. Valve 220 provides valve connector 315 from the same elastomeric material as actuating element 305 and provides valve coupler 325 from the same rigid plastic material as external housing shell 310. As illustrated further, external housing shell 310 is implemented as a pair of symmetric half-shells that contain and encapsulate actuating element 305 in a tight-fitting manner. Connecting hose connector 125 to valve coupler 325, in addition to "snap fitting" internal matching grooves with respect to external rings of actuating element 305 and actuating buttons 320 extending through apertures 330, helps to maintain the pair of half-shells closed.

Also illustrated in FIG. 3 is a pair of optional lips 340, each lip 340 corresponding to one actuating button 320 and associated with a perimeter of aperture 330. Lips 340 may be used to limit a distance that the corresponding actuating button 320 can travel when depressed. This feature, collectively, ensures that no actuating button 320 on its own can completely close collapsible air channel 335, even when completely closed and abutting lip 340.

Figure 4:
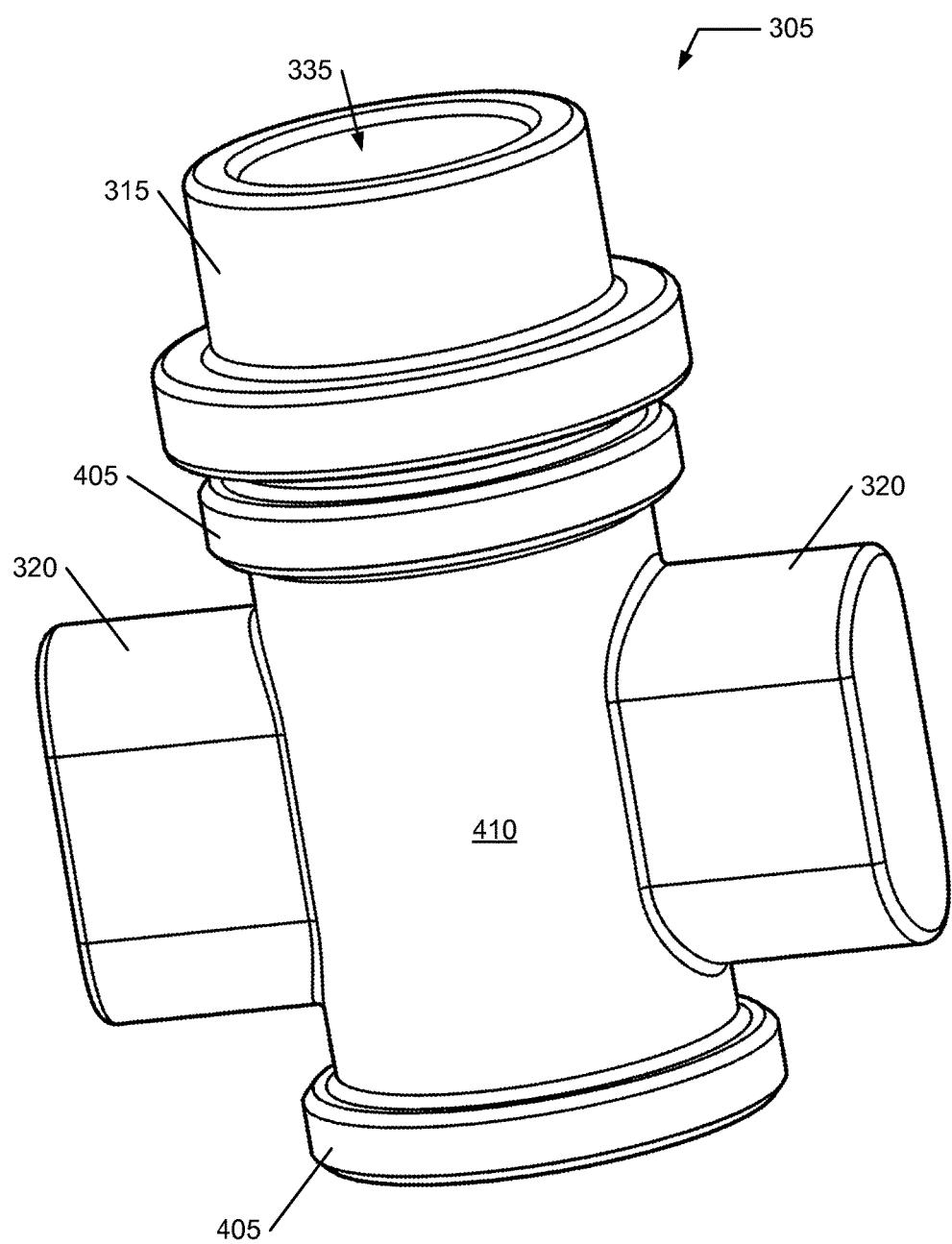
FIG. 4 illustrates a perspective view on the actuating element of the improved PAPT airflow valve of FIG. 3.

FIG. 4 illustrates a perspective view on actuating element 305 of the improved PAPT airflow valve of FIG. 3. Actuating element 305 is a single, molded, elastomeric, generally cylindrical structure that includes a pair of external rings 405 for helping to seal to external housing shell 310, and actuating buttons 320 to selectively and repeatably control air flow. Collapsible air channel 335 extends longitudinally completely through actuating element 305. The elastomeric material used to make actuating element 305 is "biased" so that collapsible air channel 335 is open and unobstructed. When a body portion 410 of actuating element 305 is collapsed by laterally forcing actuating buttons 320 together, collapsible air channel 335 collapses and closes to temporarily suspend air flow through actuating element 305. Releasing actuating buttons 320 automatically and fully reopens collapsible air channel 335 without user intervention to restore air flow through actuating element 305.

Figure 5:
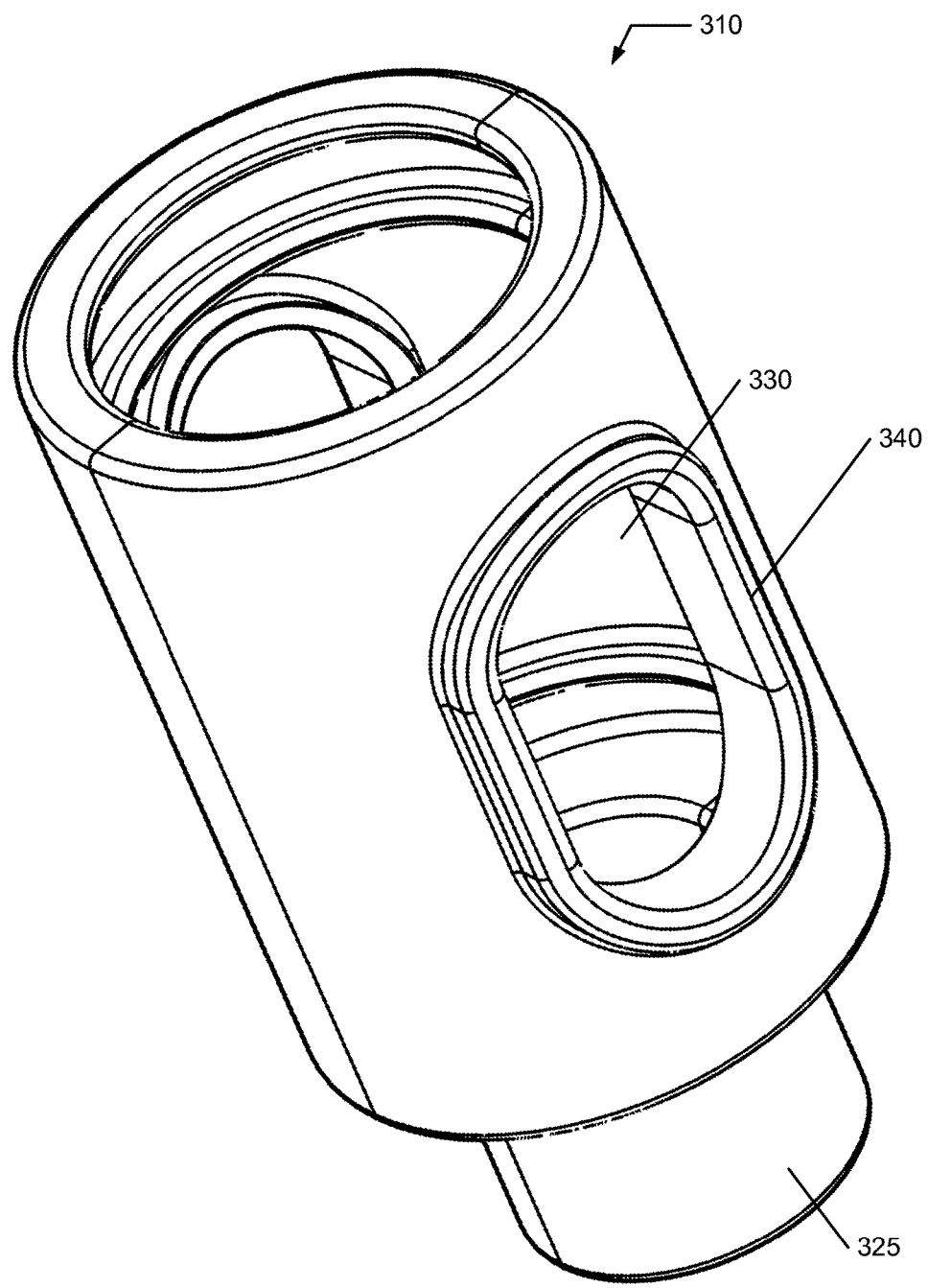
FIG. 5 illustrates a perspective view of the external housing shell of the improved PAPT airflow valve of FIG. 3.
Figure 6:
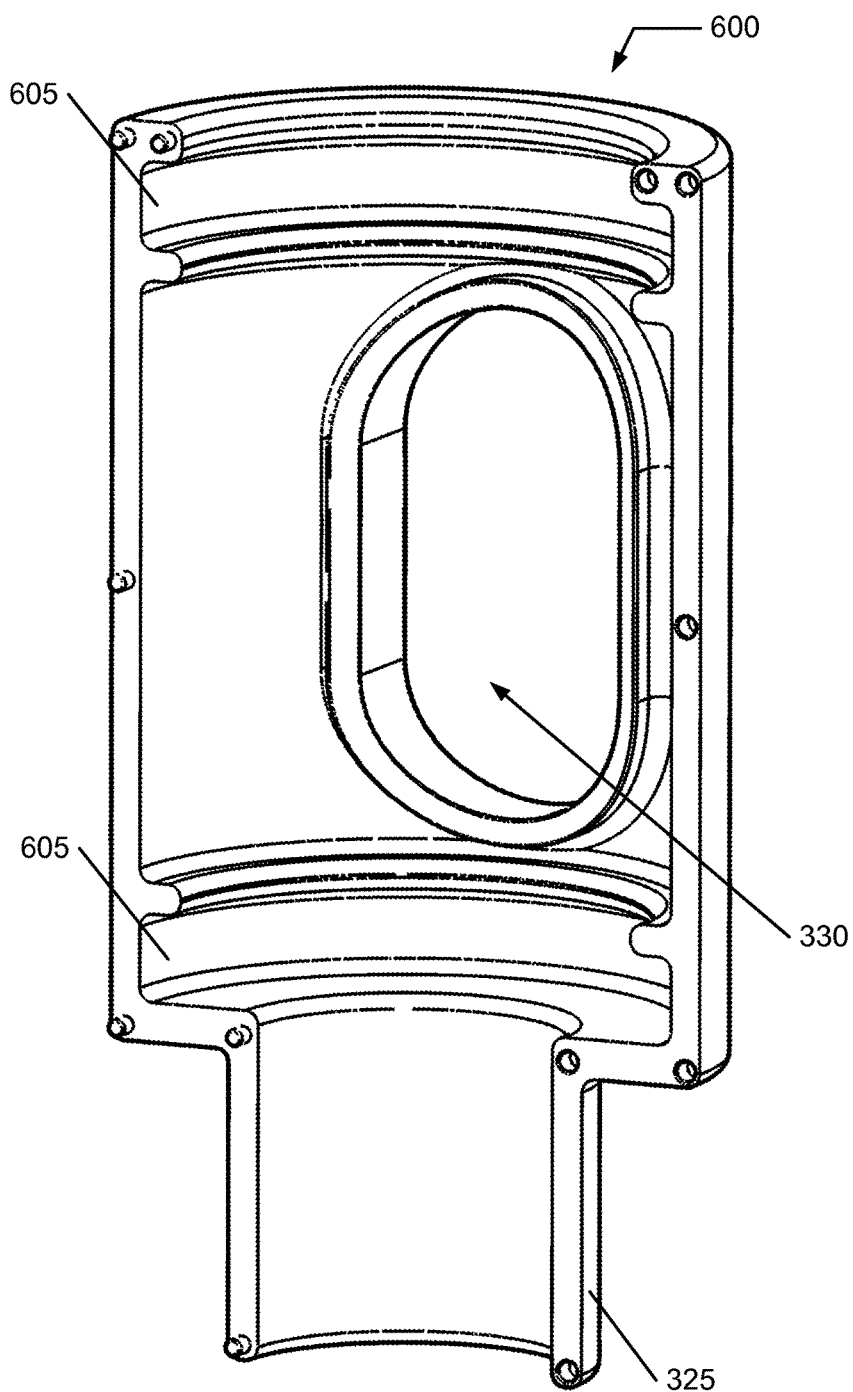
FIG. 6 illustrates a sectional view of the external housing shell illustrated in in FIG. 5.

FIG. 5 illustrates a perspective view of external housing shell 310 of the improved PAPT airflow valve of FIG. 3. FIG. 6 illustrates a sectional view of external housing shell 310 illustrated in in FIG. 5. External housing shell 310 is formed from a pair of mirror-image half-shells 600. Each half-shell 600 includes a pair of internal grooves 605 that are complementary to the pair of external rings 405 of actuating element 305. When actuating element 305 is installed in the pair of half-shells 600, actuating buttons 320 extend through apertures 330. Additionally, rings 405 seat within grooves 605 to provide an air tight seal between actuating element 305 and external housing shell 310 as there is an interface required to couple air from hose 120 passing through valve coupler 325 and entering into collapsible air channel 335. The elastomeric material, particularly rings 405, function as integrated "O ring" seals.

Figure 7:
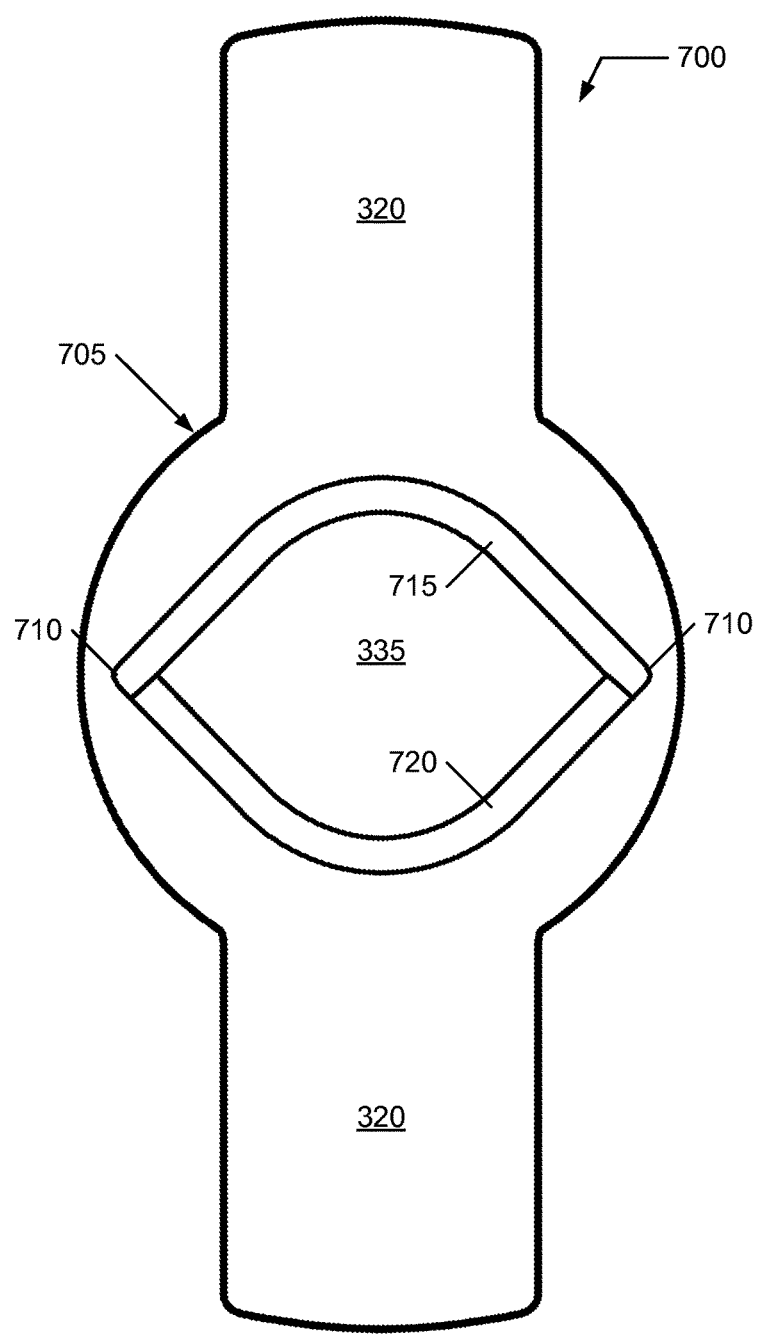
FIG. 7 illustrates an internal sectional end view of the actuating element.

FIG. 7 illustrates an internal sectional end-view 700 of a segment 705 of actuating element 305 illustrated in FIG. 4. The section is taken through a body portion of actuating element 305 located where actuating buttons 320 are coupled to collapsible air channel 335. Segment 705 is provided with a couple of optional internal structures that improve performance and reliability. These optional internal structures include one or more of a pair of hinging notches 710 laterally opposed across a sealing diameter of the generally circular collapsible air channel 335, and a first pair of ribs 715 that interleave with a second pair of ribs 720 when collapsible air channel 335 begins to collapse and close. This sealing diameter is preferably at right angles to a diameter joining the opposing actuating buttons 320. Each set of ribs includes a group of semi-circle ridges forming alternating peaks and valleys, with peaks of one set of ribs longitudinally aligned with valleys of the other set of ribs. The number of ribs in a set may vary, from the simplest of one rib in each set, to two ribs in one set and a single rib in the other, to combinations up 10 or more ribs in each set.

Hinging notches 710, as further explained below, provide an integrated living hinge that permits opposing walls of segment 705 to flatten and come together to seal collapsible air channel 335, with the help of the ribs as they interleave together. The wall thicknesses and diameter of the components, particularly the walls of segment, are configured to be stiff enough to bias the collapsible air channel open, stiff enough to not accidentally close, but pliable enough to be easily squeezed and closed off. Notches 710 improve squeezability and sealing fidelity of actuating element 305.

Figure 8:
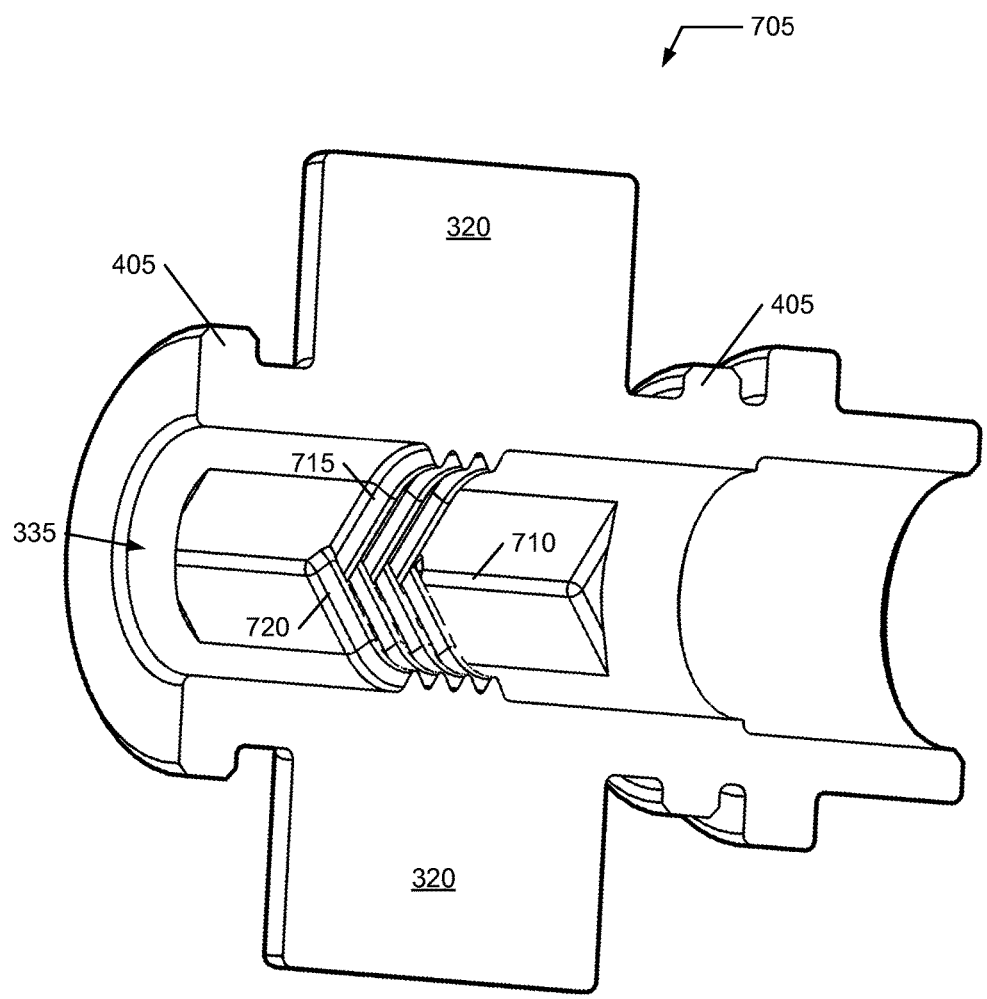
FIG. 8 illustrates a sectional side view of the actuating element.

FIG. 8 illustrates a side-view of segment 705 of actuating element 305 illustrated in FIG. 7. In FIG. 8, first set of ribs 715 includes 5 semicircular ribs and second set of ribs 720 includes 4 semicircular ribs longitudinally offset from the first set of ribs. This enables the ribs to interleave as collapsible air channel 335 collapses and closes, hinging about notches 710.

Figure 9:
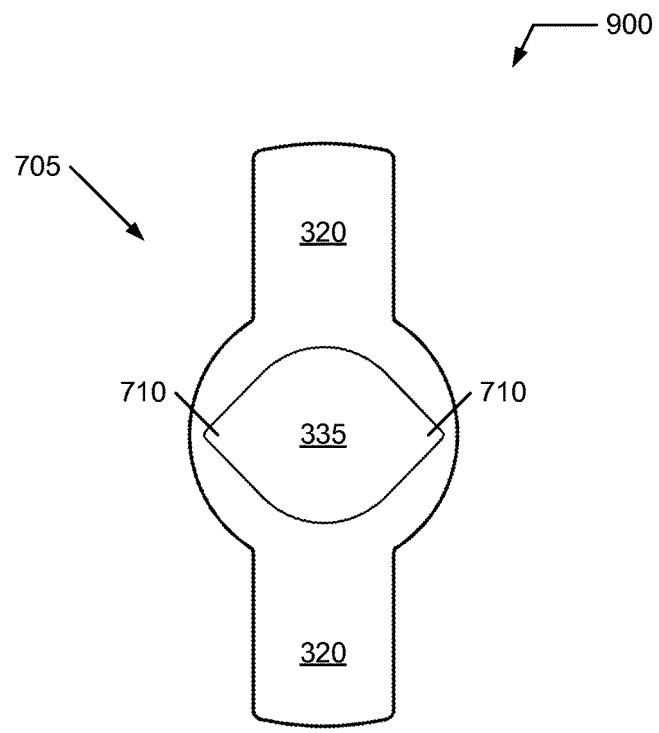
FIG. 9 illustrates a schematic sectional end view of the actuating element of FIG. 7 without the interlocking ribs.
Figure 10:
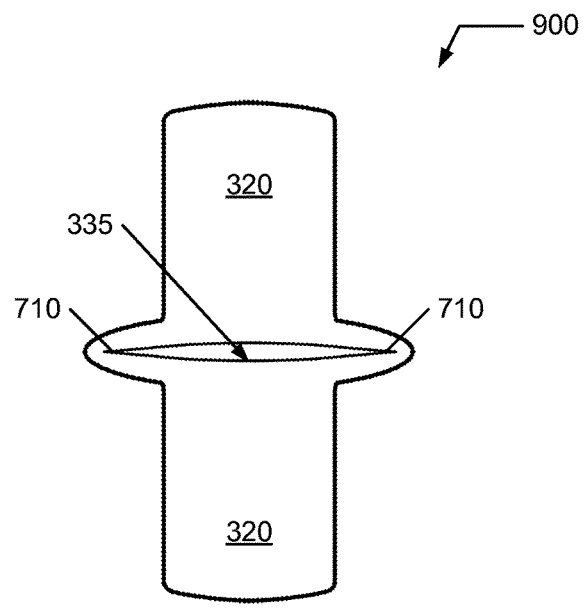
FIG. 10 illustrates a schematic sectional end view of a collapse of the actuating element of FIG. 9.

FIG. 9 illustrates an end-view of 900 similar to end-view 700 of FIG. 7 without the sets of interlocking ribs. FIG. 10 illustrates a representative schematic end-view of a collapse of the actuating element of FIG. 9 by opposing compression of actuating buttons 320. Some implementations will not require one or both sets of ribs as collapsible air channel 335 in FIG. 10 will be completely closed without them. Alternatively, air channel 335 may be partially open (and substantially closed) while restricting air flow sufficiently to enable comfortable speech. The sets of ribs will improve the ease and completeness of closure in some implementations. To inhibit any annoyance or distraction from low flowrate air flow or associated sounds from such air flow during closure, the easier and more complete the closure of collapsible air channel 335 the better.

In operation, valve 220 begins with actuating element 305 (and its associated collapsible air channel 335) in the fully open mode illustrated in FIG. 7 and FIG. 9. When the user squeezes both opposing actuating buttons 320, valve 220 closes by transitioning to the collapsed mode illustrated in FIG. 10

Figure 11:
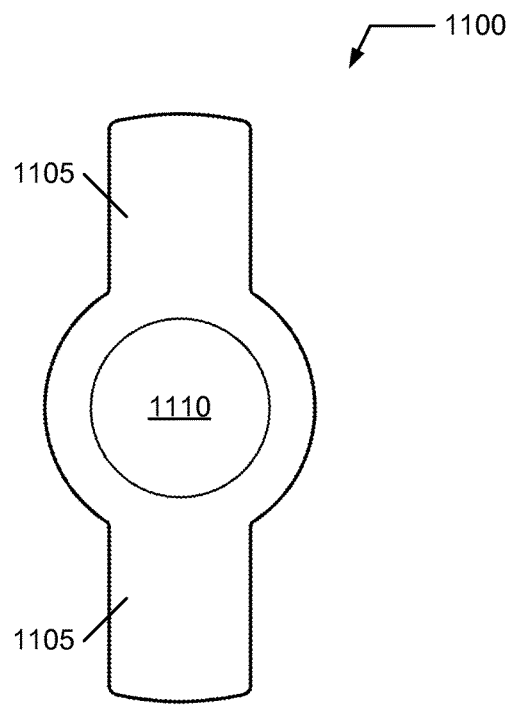
FIG. 11 illustrates a schematic sectional end view of an actuating element lacking the hinging structure of FIG. 7.
Figure 12:
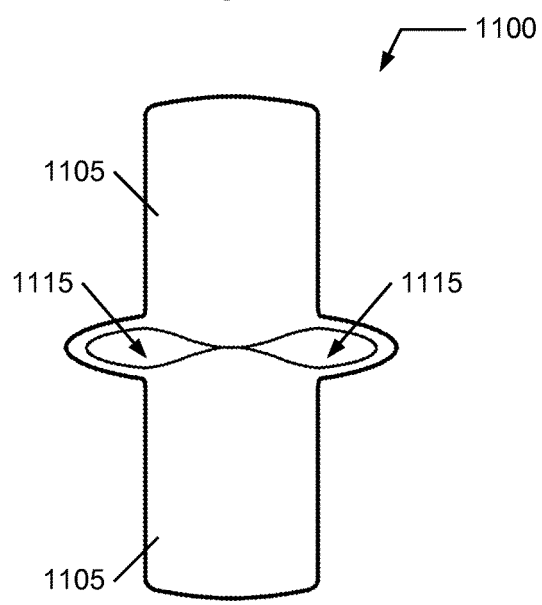
FIG. 12 illustrates a schematic sectional end view of a collapse of the actuating element of FIG. 11.

FIG. 11 illustrates an end-view 1100 of an actuating element lacking the hinging and rib structures of FIG. 7; and FIG. 12 illustrates a representative schematic end-view of a collapse of the actuating element of FIG. 11. When the construction materials and wall thicknesses are such as to be biased open and resist premature closure, actuating opposing buttons 1105 does not close an air channel 1110. Rather than close, the walls of the actuating element buckle in the middle to divide channel 1110 and present a pair of air channels 1115. These channels 1115 are unable to reliably close and suspend air flow in response to actuation of buttons 1105.

While in some implementations, it is possible to configure valve 220 to operate with a single actuating button to close collapsible air channel 335. However, to inhibit a user from accidentally triggering and actuating valve 220, such by rolling over on the button or other sleep time manipulation, the disclosed valve 220 is preferred to have a pair of opposing actuating buttons that must be purposefully and concurrently actuated in order to suspend air flow. One way to do this is to configure a relative length of the actuating buttons and housing shell thickness so that both actuating buttons must both be completely depressed (pressed to housing shell surface) to close the air flow. The user must consciously actuate valve 220 as it is difficult to accidentally operate which improves user safety. With the safety features described herein, it is extremely difficult to accidentally and unintentionally close valve 220.

By providing valve 220 as a user serviceable/cleanable simple assembly with minimal components, a single piece actuating element and a housing having a pair of half-shells containing the actuating element, the user is able to simply and confidently clean it. Further, there are no mechanical moving parts requiring assembly or wearing on other parts that could fail. The embodiments illustrated and described herein do not present or introduce any exposed opening to the air flow path from pressure generator 210 to PAPT mask 205 and are therefore safer than any valve that provides an exposed opening.

Figure 13:
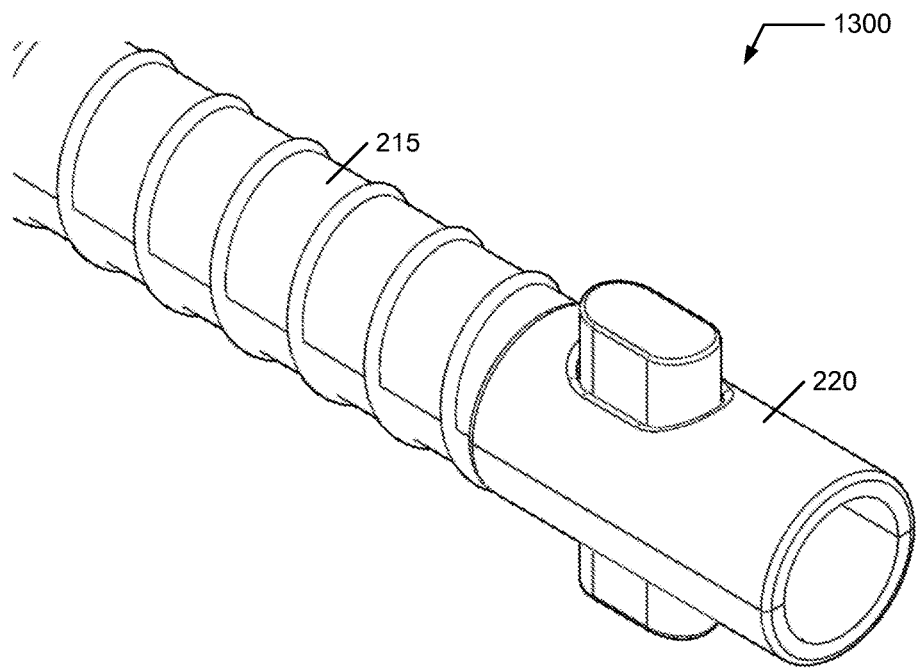
FIG. 13-FIG. 17 illustrate representations of various types of integrations of a PAPT airflow valve.
Figure 14:
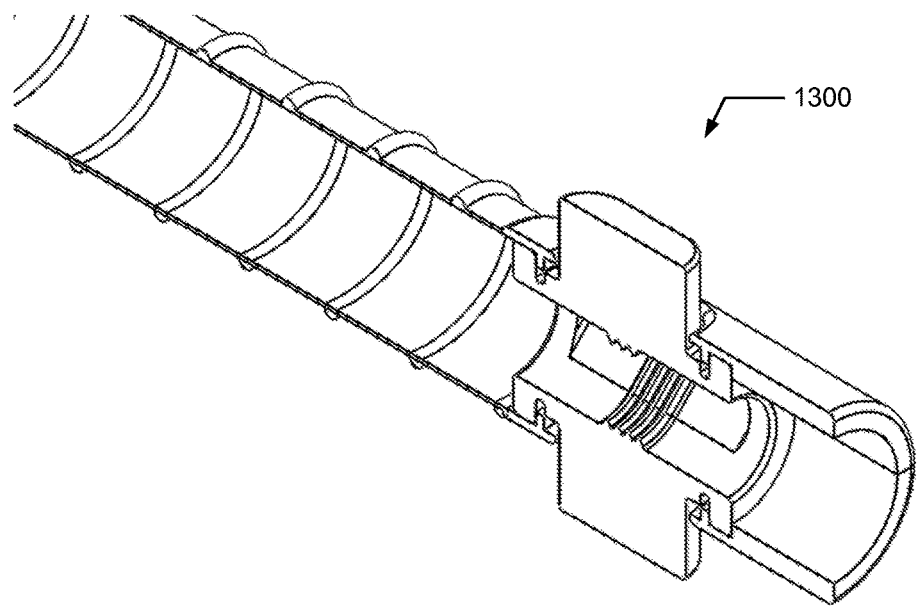

FIG. 13-FIG. 17 illustrate representations of various types of integrations of a PAPT airflow valve 220, with FIG. 13 and FIG. 14 illustrating an integration assembly 1300 of PAPT airflow valve 220 with pressure delivery structure 215. FIG. 13 illustrates an outline of integration assembly 1330 with pressure delivery structure 215 and FIG. 14 illustrates a longitudinal sectional view of integration assembly 1300 illustrated in FIG. 13.

Figure 15:
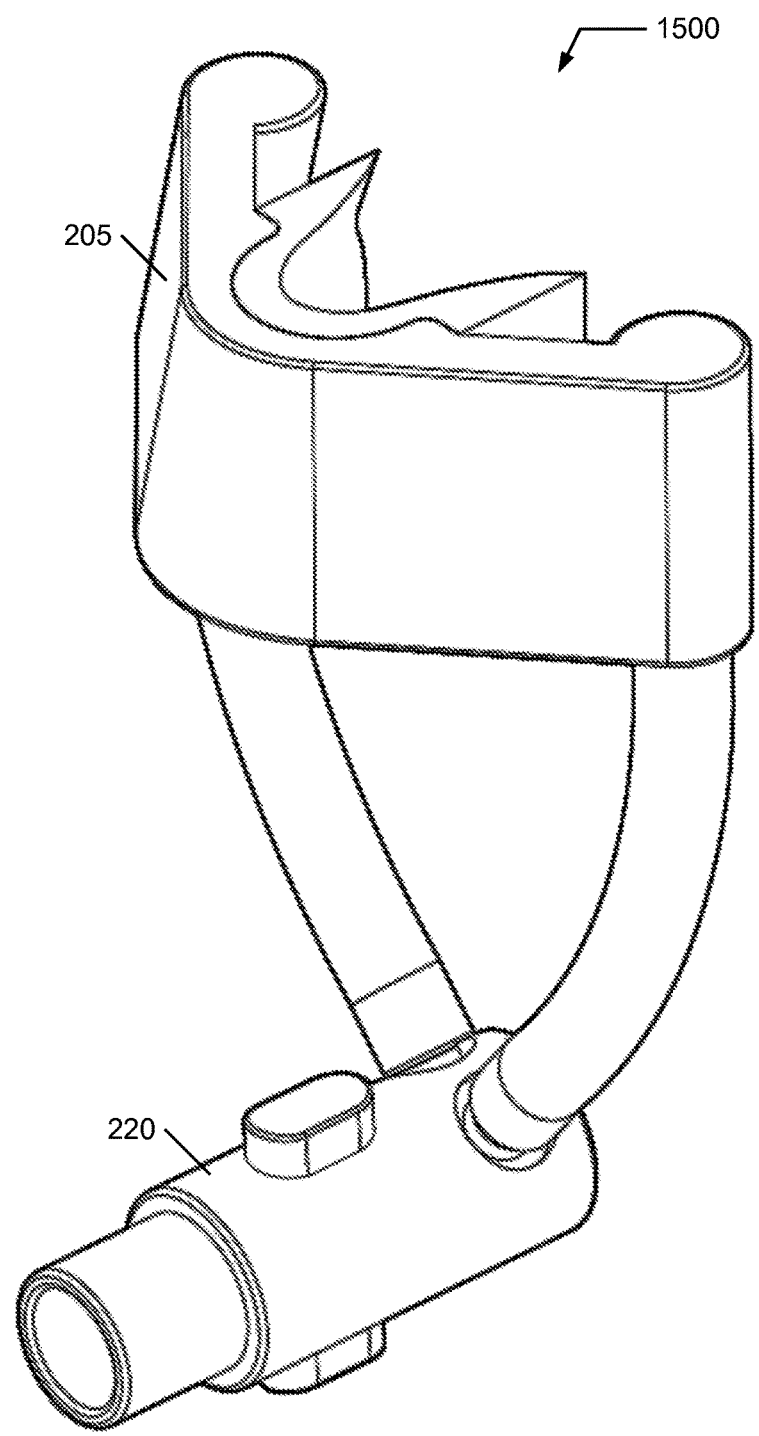
Figure 16:
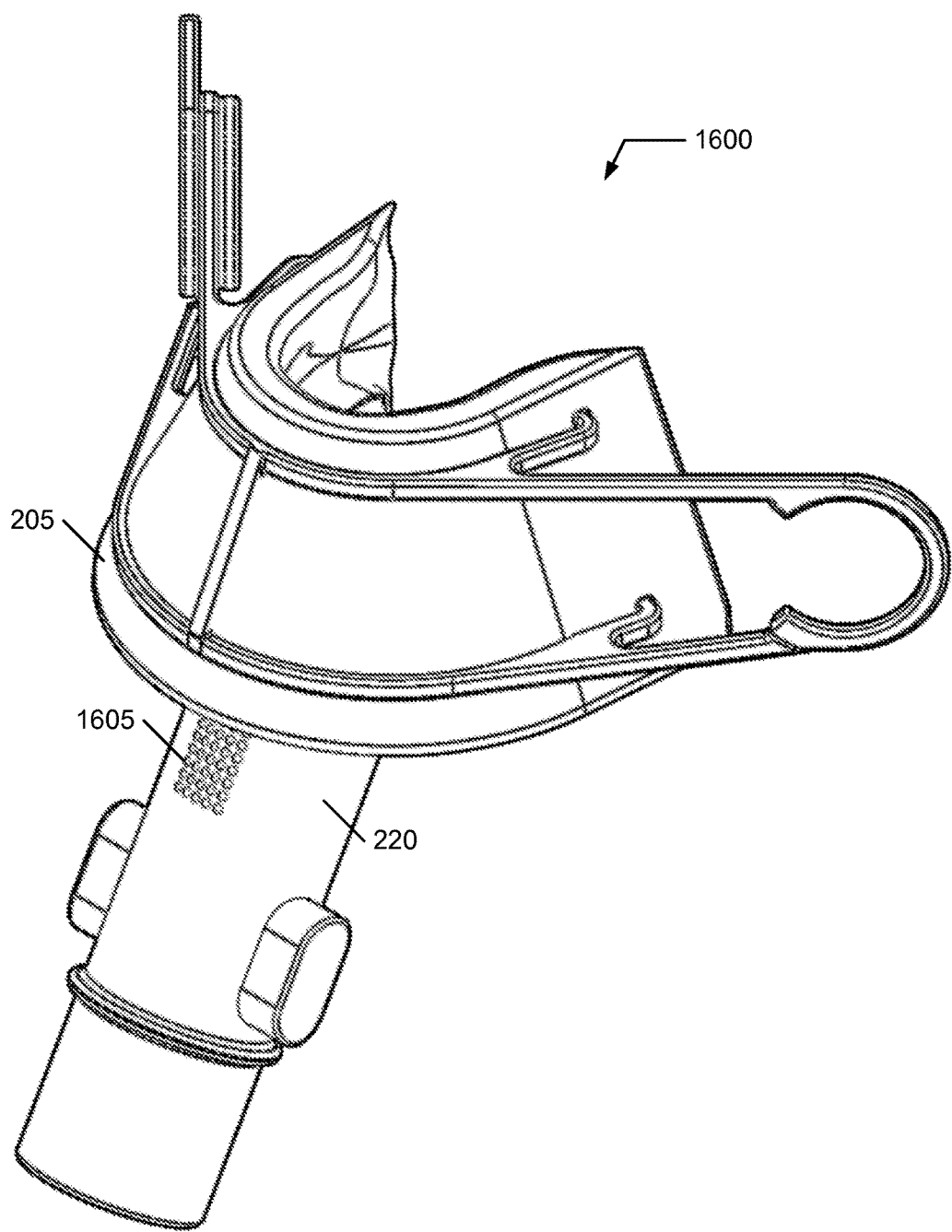
Figure 17:
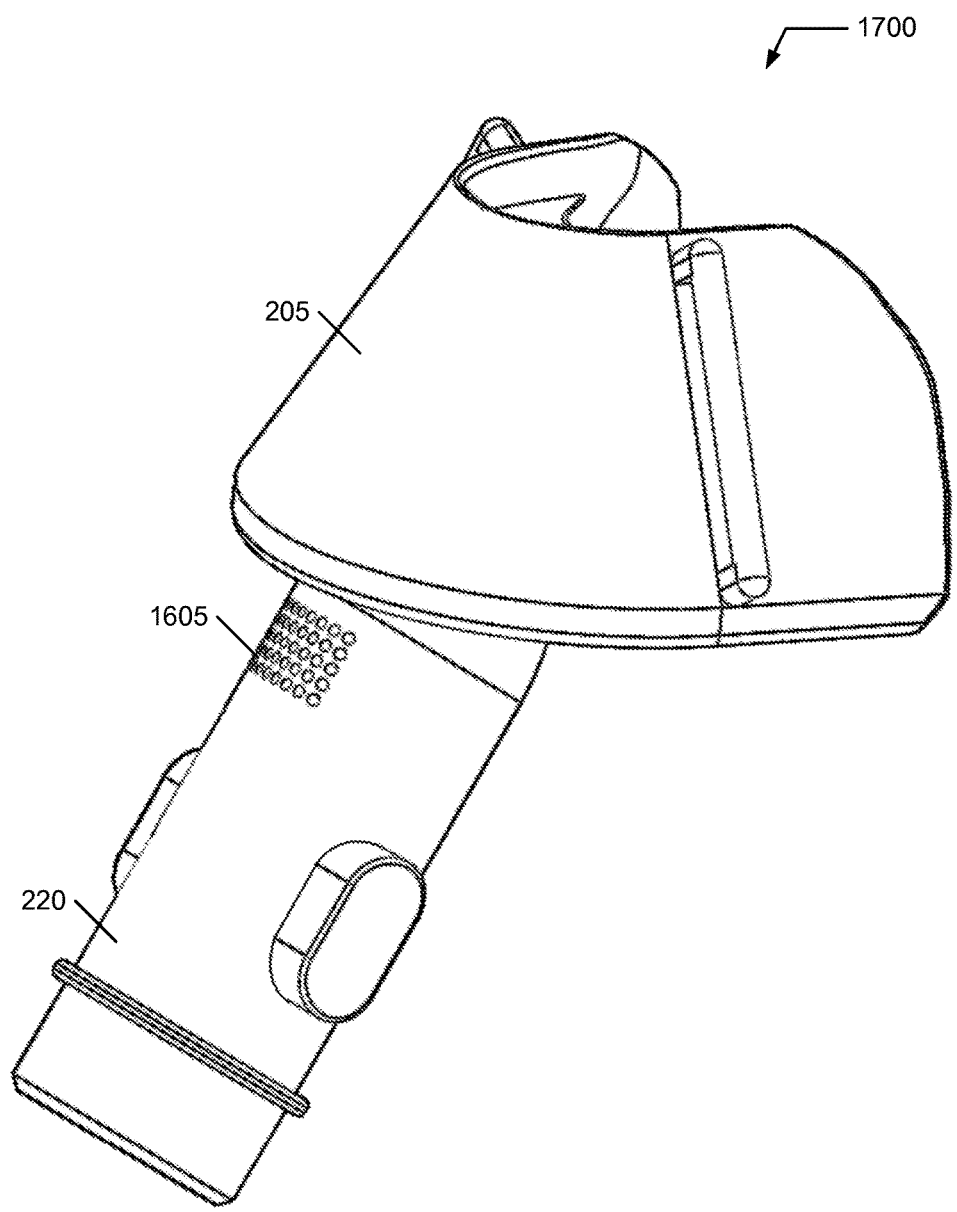

FIG. 15-FIG. 17 illustrate an integration assembly of PAPT airflow valve 220 with different mask implementations. FIG. 15 illustrates an outline of an integration assembly 1500 with a first mask style 205; FIG. 16 illustrates an outline of an integration assembly 1600 with a second mask style 205; and FIG. 17 illustrates an outline of an integration assembly 1700 with a third mask style 205.

In some implementations, it may be necessary or desirable to include one or more apertures (e.g., an array of apertures) 1605 that are communicated to the pressurized air channel. Apertures 1605 serve as an over pressurization regulation mechanism to prevent or inhibit over pressurization during operation. When present, some implementations may optionally dispose them in PAPT valve 220 or other location.

Figure 18:
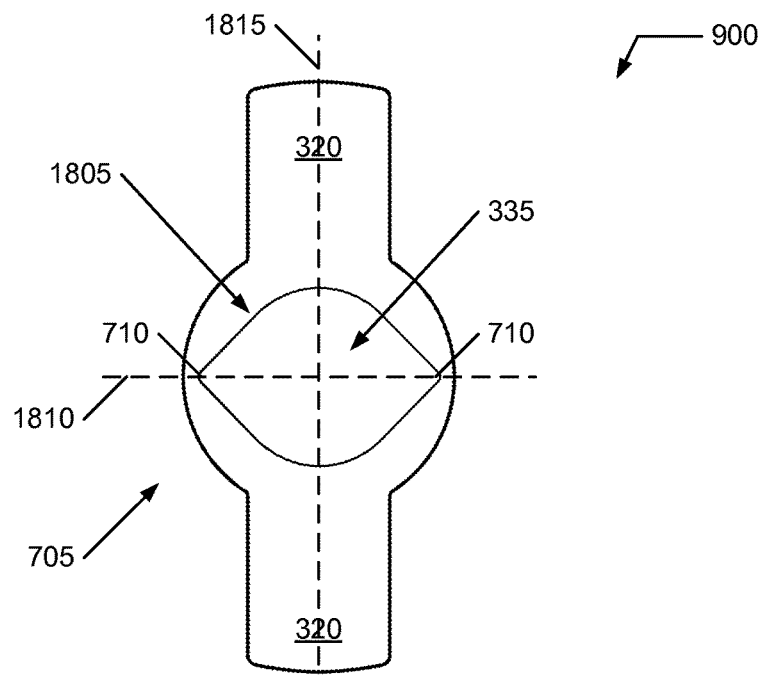
FIG. 18 and FIG. 19 further describe a configuration and operation of an "eye" shaped air channel.
Figure 19:
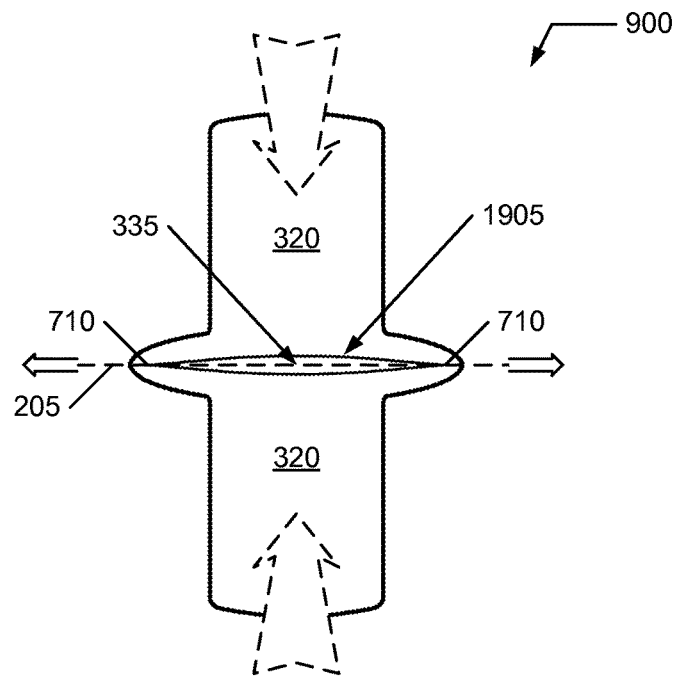

FIG. 18 illustrates a schematic sectional end view of the actuating element of FIG. 7 without the interlocking ribs; and FIG. 19 illustrates a schematic sectional end view of a collapse of the actuating element of FIG. 18 (and incorporates the discussion associated with FIG. 9 and FIG. 10. FIG. 18 is included to further explain a preferred implementation of air channel 335. As discussed herein, actuating element 305 is illustrated as a single unitary structure made from an elastomeric material that provides resilience and elasticity to the structure. The resiliency provides a mechanism by which air channel 335 is biased open, which means that when any actuating force is removed from buttons 320, air channel 335 automatically reopens and returns to the "eye" shaped cross-section 1805 as illustrated.

Actuating element 305 includes a collapsible wall as part of the air tight communication channel that extends from a proximal end to a distal end. FIG. 18 and FIG. 19 illustrate a portion of that communication channel where a valving control is defined. At this portion, an interior perimeter is preferably shaped into this "eye" shaped cross section 1805 contour. In FIG. 18 and FIG. 19, the air communication channel of the portion extends perpendicularly into and out of the cross section. A lateral axis 1810 extends between hinging notches 710. Eye shaped section 1805 is substantially symmetric about lateral axis 1810 with hinging notch 710, such as illustrated with a pair of opposing actuators.

Actuating element 305 includes an actuating axis 1815, perpendicular to lateral axis 1810. Buttons 320, each button an integrated portion of the collapsible wall defining air channel 335, are aligned with actuating axis 1815. Buttons 320 move along actuating axis 1815 when collapsing to close, or substantially restrict air flow through this portion of actuating element 305. Eye-shaped section 1805 is also symmetric about actuating axis 1815. Eye-shaped section 1805 includes a set of relatively straight segments extending from hinging notches 710 which meet at a curved intermediate apex. While there are many different profiles that may be implemented for the cross section contour, the result achieved among these devices will be substantially equivalent. Eye-shaped section 1805 is a mechanism whereby an air channel defined in a tubular collapsible elastomeric wall may be automatically biased wide-open and collapsed to sufficiently close the air channel where speech is possible.

When collapsed, air channel 335 defines a closed contour 1905. Note that the nature of this unitary elastomeric structure, as buttons 320 close, lateral edges of actuating element 305 (portions near hinging notches 710) move further apart. The curved apex portions of eye-shaped section 1805 flatten and extend, allowing the closed contour to have substantially parallel upper and lower wall segments which allow air channel 335 to inhibit/obstruct and/or stop air flow.

Figure 20:
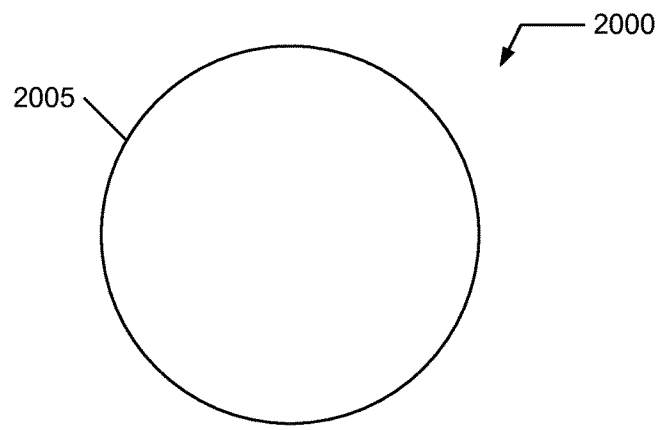
FIG. 20-FIG. 22 illustrate a representative series of steps in a definition of the eye-shaped section.
Figure 21:
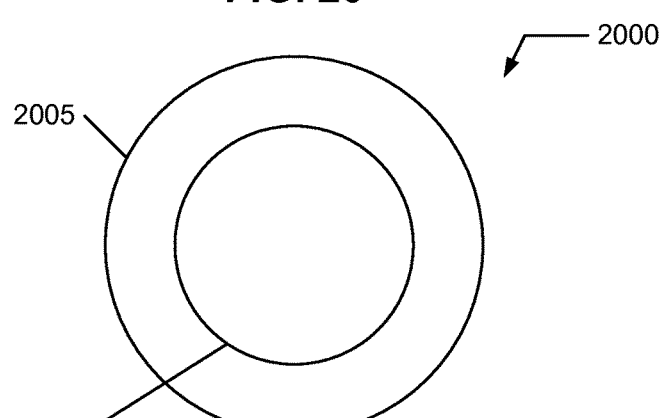
Figure 22:
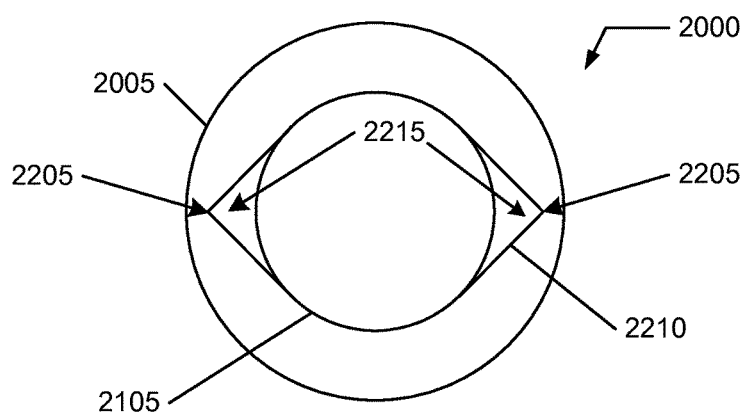

FIG. 20-FIG. 22 illustrate one process for forming a representative eye-shaped section 2000 illustrated and described herein. FIG. 20 illustrates a cross section of an elastomeric structure 2005. Structure 2005 is illustrated as having a circular outer surface but as noted, other exterior surfaces are possible including regular or irregular polygons having N number of sides (N=3 to 10 or more), ellipses, and other conic or curved surfaces, and combinations thereof. A central air channel is formed creating a tube, such as by defining an interior cavity. The cavity is formed by defining an interior perimeter contour inside structure 2005. The contour for the eye-shaped section is a modified circular contour in which a suitable circular perimeter 2105 for the cavity is initially specified as illustrated in FIG. 21.

Circular perimeter 2105 is modified to form the eye-shaped section such as by locating a pair point vertices 2205 that will become apexes of hinging notches 710 and extending four line segments 2210; two from each vertex 2205 towards the perimeter 2105, with line segments 2210 being substantially tangent to perimeter 2105 where they intersect. The regions 2215 are "removed" from the design leaving the eye-shaped section contour illustrated and described herein. As noted, other strategies and designs for a suitable interior perimeter are possible to define an automatically opening closable valving structure implemented in a unitary elastomeric structure.

In certain ones of the illustrated embodiments, a rigid outer shell is described and presented. The implementation of such an outer shell is a secondary aspect of the present invention. A primary aspect of the invention includes the use of a unitary flexible elastomeric actuating element. This actuating element is illustrated as a structure including a generally cylindrical flexible tube having a central air channel extending through a flexible collapsible wall. The structure includes at least one interior portion provided with a valving surface. The valving surface is implemented at the interior portion where an exterior wall is collapsible. The valving surface implements a perimeter shape that is wide open when the collapsible wall automatically returns to an unactuated mode. The perimeter shape is chosen such that, when distortions of the flexible wall responsive to its collapse are accounted, the actuated perimeter is able to close or substantially close the central air channel and sufficiently stop air flow. A preferred implementation of this perimeter shape to achieve these characteristics is the disclosed "eye-shaped" section. When actuated, the perimeter shape flattens, partially responsive to the hinging notches positioned at vertices of the eye-shape. Other perimeter shapes are possible to achieve these characteristics including those based upon a series of straight line segments, and do not necessarily need to be based upon a circular template. The perimeter need not be symmetric about the lateral axis, for example in the event that a single actuator is implemented. An outside surface without an actuator may enable the corresponding proximate inner surface to be relatively flat and interoperate with a contoured moving/collapsing opposing inner surface proximate the outside surface having the actuator.

In some instances, it may be necessary or desirable to add ribs to the interior surface. A simple implementation includes a pair of ribs, one on each facing and mating inner wall surface. These ribs are preferably implemented in sets of complementary ribs that are interleaved when the inner perimeter is collapsed and the air channel closed. The ribs may serve not only a function to help further stop air flow, in some cases it may help in reducing vibratory sounds that can result from air flowing in the air channel when the flexible wall is partially or wholly collapsed.

While the illustrated embodiments provide for the valving surface to implemented in one localized portion, some alternate implementations may include multiple valving surfaces. For example, when integrated into an air pressure delivery hose, there may be valving surfaces disposed toward each end of the hose which may have several advantages, including improving installation options by making the hose symmetric and having an actuating element near the mask no matter which end of the hose is attached to the mask. In some implementations, the entire length of the delivery hose or hose segment may be provided with valving structures so the user or other operator helping the user may simply squeeze the hose at any location.

While the basic structure of the actuating element is described as being "tubular" it is not necessary that the outer surface be The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letter Patent of the United States is:

1. A positive airway pressure valve used in a treatment of a breathing disorder, comprising:
    an actuating element having an elongate unitary structure including a collapsible elastomeric wall extending from a distal end to a proximal end, said collapsible elastomeric wall defining an interior air channel extending from said proximal end to said distal end and configured for repeatable transitions between an open mode and a collapsed mode with said collapsible elastomeric wall biased to said open mode and configured to automatically return to said open mode when released from said collapsed mode, said interior air channel including an interior portion wherein said interior portion consisting essentially of a pair of opposing hinge notches configured to form a living hinge and wherein said interior portion further consists essentially of a pair of opposing interior wall segments divided by said pair of opposing hinge notches with said opposing interior wall segments configured to be separated from each other when said collapsible wall is in said open mode and configured to be proximate and mate to each other along a line extending between said hinge notches to substantially obstruct said interior air channel when said collapsible wall is in said collapsed mode;
    wherein said elongate unitary structure includes a longitudinal axis extending generally parallel to said interior air channel and wherein said pair of opposing wall segments includes a first wall segment and a second wall segment and further comprising a first set of one or more ribs disposed on said first wall segment and a second set of one or more ribs disposed on said second wall segment, said first set of ribs complementary to said second set of ribs and with said sets of ribs configured to close said interior air channel when said collapsible wall is in said collapsed mode, wherein said ribs of said sets of one or more ribs extend parallel a rib axis extending between said hinge notches with said rib axis generally perpendicular to said longitudinal axis.

2. The positive airway pressure treatment airflow valve of claim 1 further comprising:
    an exterior rigid shell including a pair of rigid half-shells coupled to and enclosing said actuating element.

3. The positive airway pressure valve of claim 1 wherein said hinge notches are 180 degrees apart and define a living hinge line extending therebetween that is perpendicular to said interior air channel at said interior portion, said collapsible elastomeric wall defining a pair of exterior opposing actuator buttons each proximate said interior portion and extending away from said collapsible elastomeric wall in different opposing directions along a line perpendicular to said living hinge line and to said interior air channel at said interior portion.

4. The positive airway pressure treatment airflow valve of claim 3 further comprising:
    an exterior rigid shell including a pair of rigid half-shells coupled to and enclosing said actuating element, each said half-shell including an aperture receiving one of said actuator buttons.

5. The positive airway pressure treatment valve of claim 1 wherein said ribs of said first set of one or more ribs interlock with said ribs of said second set of one or more ribs to obstruct said air channel.

6. The airflow valve of claim 5 wherein said sets of ribs define longitudinally extending series of alternating complementary peaks and complementary recesses collectively configured to interlock in said collapsed mode.

7. An airflow valve used in a positive airway pressure treatment of a breathing disorder, comprising:
    a unitary elongate elastomeric structure including a proximal end having a proximal opening, a distal end having a distal opening, a flexible side wall extending between said ends with said side wall including an inner wall surface defining an air channel extending along a longitudinal axis extending between said openings; wherein a portion of said inner wall surface between said ends defines a valving surface, said valving surface having an eye-shaped section including a pair of hinging notches;

wherein a hinge notch line extends between said pair of hinging notches;

wherein said valving surface includes a pair of valving surface portions including a first valving surface portion opposing a second valving surface portion, each said valving surface portion extending perpendicular to said longitudinal axis from a first hinging notch of said pair hinging notches to a second hinging notch of said pair of hinging notches;

wherein said unitary elongate elastomeric structure includes an open mode wherein said air channel is substantially unobstructed by said valving surface portions and further includes a collapsed mode wherein said air channel is substantially obstructed by said valving surface portions;

wherein said opposing valving surface portions mate in said collapsed mode along said hinge notch line;

wherein said valving surface further includes at least one pair of opposing complementary ribs, said at least one pair of opposing complementary ribs extending parallel to a lateral axis perpendicular to said longitudinal axis.

8. The airflow valve of claim 7 further comprising:
an exterior rigid shell including a pair of rigid half-shells coupled to and enclosing said unitary elongate elastomeric structure.

9. The airflow valve of claim 7 wherein said hinging notches are opposite each other along a lateral axis perpendicular to said longitudinal axis, wherein said side wall includes an exterior wall surface portion proximate said inner wall surface defining an actuator portion of said side wall, and wherein said side wall includes at least one actuator extending from said actuator portion along an actuator axis perpendicular to said lateral axis and perpendicular to said longitudinal axis.

10. The airflow valve of claim 9 wherein said side wall includes a pair of opposing actuators, further comprising:
an exterior rigid shell including a pair of rigid half-shells coupled to and enclosing said unitary elongate elastomeric structure, each said half-shell including an aperture receiving one of said actuators of said pair of actuators and wherein each said actuator includes a length, wherein each said half-shell includes a thickness, wherein said length is greater than said distance, and wherein each said actuator of said pair of actuators extend outside of said half-shells.

11. The airflow valve of claim 7 wherein said ribs of said first set of one or more ribs interlock with said ribs of said second set of one or more ribs in said collapsed mode to obstruct said air channel.

12. The airflow valve of claim 11 wherein said sets of ribs define longitudinally extending series of alternating complementary peaks and complementary recesses collectively configured to interlock in said collapsed mode.

13. An airflow control method for controlling an air flow within an air channel defined through an actuating element used in a positive airway pressure treatment of a breathing disorder, the air channel extending along a longitudinal axis, comprising:

(a) collapsing, responsive to an actuation of a flexible wall portion of the actuating element, the air channel wherein an inner surface of the air channel proximate said flexible wall portion includes a valving surface actuated by a collapsed air channel, with said valving surface including a pair of valving surface portions with a first valving surface portion opposed to a second valving surface portion, said valving surface portiions divided by a pair of opposing hinge notches, said first valving surface portion including a first set of ribs defining a first series of longitudinally extending peaks and recesses, said second valving surface portion including a second set of ribs defining a second series of longitudinally extending peaks and valleys complementary to said first series of longitudinally extending peaks and recesses wherein said peaks from each set of ribs interlock with said recesses from each other set of ribs, wherein said ribs of said sets of one or more ribs extend parallel a rib axis extending between said hinge notches with said rib axis generally perpendicular to said longitudinal axis;

(b) obstructing the air flow through the air channel using said valving surface in said collapsed air channel; and thereafter (c) expanding automatically, responsive to a deactuation of said flexible wall portion, the air channel with said valving surface deactuated by an expanded air channel; and (d) unobstructing the air flow through the air channel including bypassing said valving surface in said expanded air channel.

\* \* \* \* \*